US011759581B2

(12) United States Patent
Power et al.

(10) Patent No.: US 11,759,581 B2
(45) Date of Patent: *Sep. 19, 2023

(54) AEROSOL DELIVERY SYSTEM

(71) Applicant: Stamford Devices Limited, Galway (IE)

(72) Inventors: Patrick Joseph Power, County Galway (IE); Jimmy Eaton-Evans, Galway (IE)

(73) Assignee: Stamford Devices Limited, Glaway (IE)

( * ) Notice: Subject to any disclaimer, the term of this patent is extended or adjusted under 35 U.S.C. 154(b) by 450 days.

This patent is subject to a terminal disclaimer.

(21) Appl. No.: 16/857,701

(22) Filed: Apr. 24, 2020

(65) Prior Publication Data

US 2020/0246558 A1    Aug. 6, 2020

Related U.S. Application Data

(63) Continuation of application No. 16/118,668, filed on Aug. 31, 2018, which is a continuation of application
(Continued)

(30) Foreign Application Priority Data

Nov. 4, 2013    (EP) ..................................... 13191432

(51) Int. Cl.
*A61M 11/02*    (2006.01)
*A61M 15/00*    (2006.01)
(Continued)

(52) U.S. Cl.
CPC ........ *A61M 11/02* (2013.01); *A61M 15/0021* (2014.02); *A61M 15/0085* (2013.01);
(Continued)

(58) Field of Classification Search
CPC ................ A61M 11/02; A61M 11/003; A61M 15/0021; A61M 15/0085; A61M 15/0023;
(Continued)

(56) References Cited

U.S. PATENT DOCUMENTS 3,518,989 A    7/1970    Seeler
3,769,973 A    11/1973    Esbenshade, Jr.
(Continued)

FOREIGN PATENT DOCUMENTS

WO    WO 2012/046220 A1    4/2012

*Primary Examiner* — Joseph D. Boecker
*Assistant Examiner* — Brian T Khong
(74) *Attorney, Agent, or Firm* — Bookoff McAndrews, PLLC

(57) ABSTRACT

A system for delivery of aerosol therapy includes a housing defining a chamber. The housing has a base, a top and a main body extending therebetween. An ambient air inlet is adjacent the base and is normally closed by an inlet valve. The housing has a patient port. Exhaled air is exhausted through valves in a mouthpiece or a face mask to prevent recirculation through the chamber which would adversely affect dose efficiencies. The housing has an aerosol port for receiving a vibrating mesh aerosol generating device. The aerosol port is located in a side of the main body of the housing for delivery of aerosol into the chamber between the inlet valve and the patient port. A boss extends upwardly from the base and is spaced-apart inwardly of the main body of the housing to define a reception space or well.

19 Claims, 8 Drawing Sheets

Related U.S. Application Data

Figure 1:
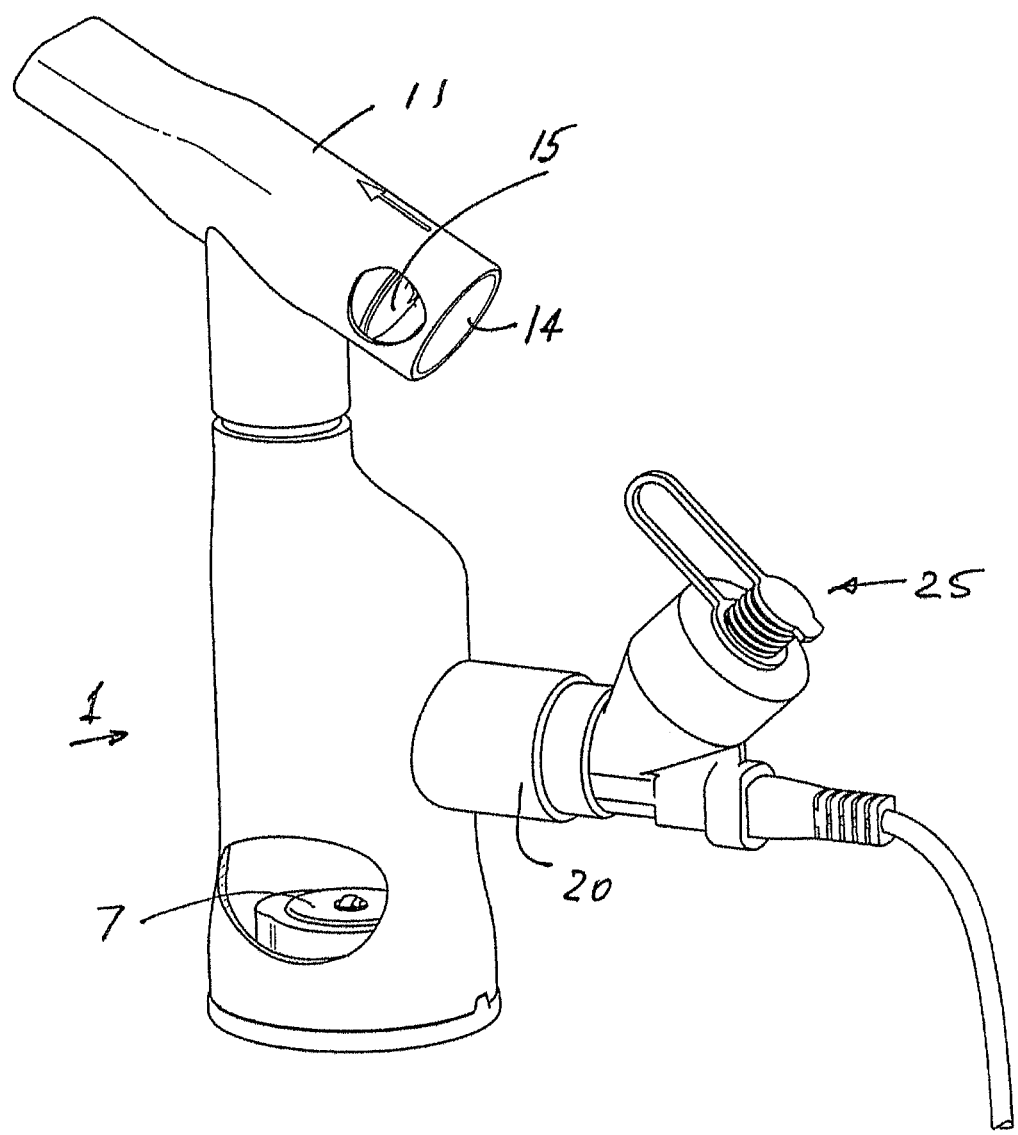
Figure 2:
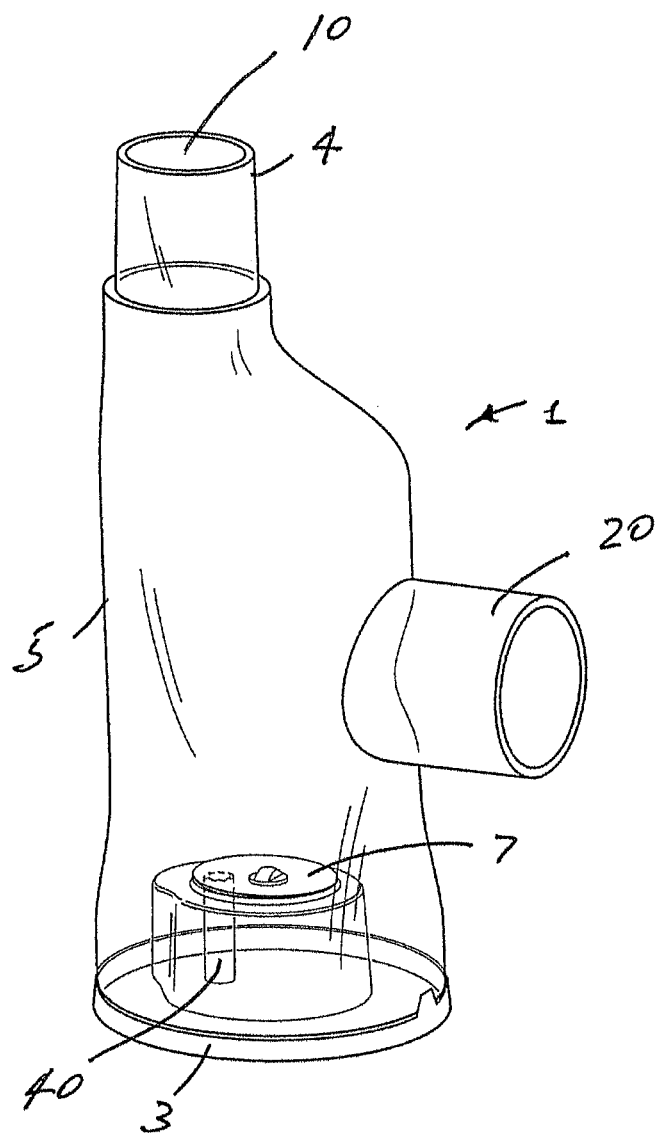
Figure 3:
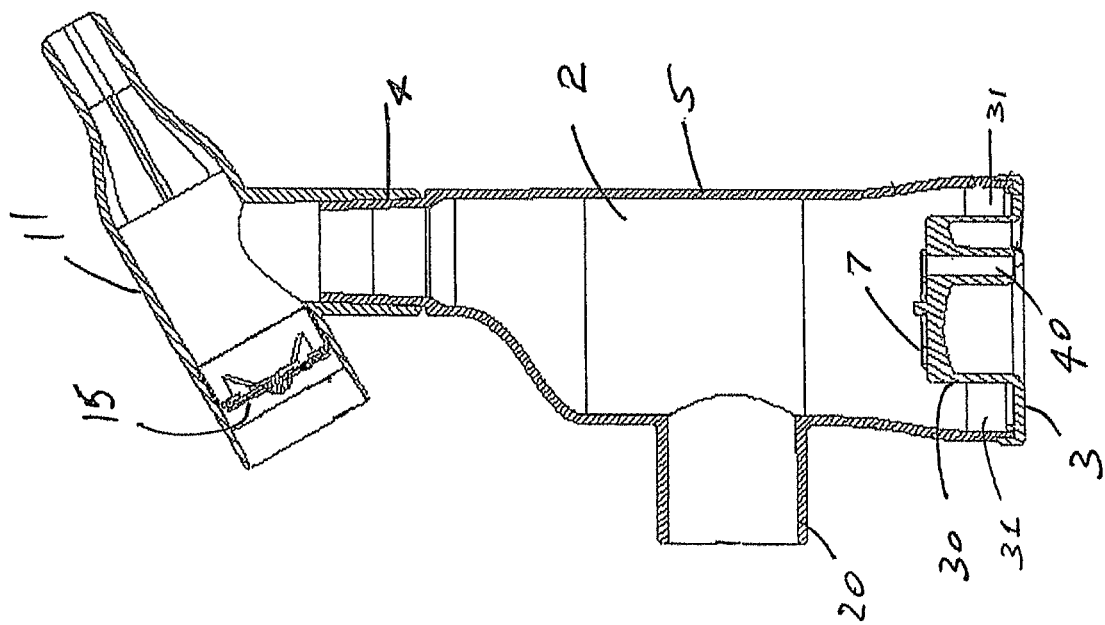

No. 14/530,173, filed on Oct. 31, 2014, now Pat. No. 10,092,712.

(51) Int. Cl.
*A61M 16/06* (2006.01)
*A61M 16/20* (2006.01)
*A61M 11/00* (2006.01)

(52) U.S. Cl.
CPC .......... *A61M 16/06* (2013.01); *A61M 16/208* (2013.01); *A61M 11/003* (2014.02); *A61M 2202/0208* (2013.01); *A61M 2202/04* (2013.01)

(58) Field of Classification Search
CPC .............. A61M 15/0025; A61M 16/06; A61M 16/208; A61M 2202/0208; A61M 2202/04
See application file for complete search history.

(56) References Cited

U.S. PATENT DOCUMENTS

| | | | |
|---|---|---|---|
| 5,540,221 A | 7/1996 | Kaigler et al. | |
| 5,617,844 A | 4/1997 | King | |
| 5,738,087 A | 4/1998 | King | |
| 6,138,668 A | 10/2000 | Patton et al. | |
| 6,176,234 B1* | 1/2001 | Salter | A61M 15/00 128/207.14 |
| 6,235,177 B1 | 5/2001 | Borland et al. | |
| 7,066,398 B2 | 6/2006 | Borland et al. | |
| 7,204,245 B2* | 4/2007 | Johnson | A61M 15/0015 128/205.24 |
| 8,151,794 B2 | 4/2012 | Meyer | |
| 2001/0013341 A1 | 8/2001 | Gallem | |
| 2002/0170557 A1* | 11/2002 | Schmidt | A61M 15/0018 128/200.23 |
| 2005/0011514 A1 | 1/2005 | Power | |
| 2005/0217666 A1* | 10/2005 | Fink | A61P 33/02 128/200.14 |
| 2006/0065267 A1* | 3/2006 | Tran | A61M 11/02 128/200.14 |
| 2006/0243274 A1* | 11/2006 | Lieberman | A61M 11/005 128/200.14 |
| 2007/0023547 A1 | 2/2007 | Borland et al. | |
| 2007/0026701 A1 | 11/2007 | Fink et al. | |
| 2011/0108025 A1* | 5/2011 | Fink | A61M 11/005 128/200.23 |
| 2012/0145148 A1 | 6/2012 | Meyer et al. | |
| 2014/0166010 A1* | 6/2014 | Varga | A61M 16/0825 128/203.29 |

\* cited by examiner

AEROSOL DELIVERY SYSTEM

CROSS REFERENCE TO RELATED APPLICATION(S)

This application is a continuation of U.S. patent application Ser. No. 16/118,668, filed Aug. 31, 2018, which is a continuation of U.S. patent application Ser. No. 14/530,173, filed Oct. 31, 2014, which claims priority from European Application No. 13191432.7, filed Nov. 4, 2013, the contents of all of which are incorporated herein by reference in their entirety.

INTRODUCTION

This invention relates to the delivery of aerosol to patients in response to spontaneous breathing.

US2011/0108025 describes an aerosol transfer device coupled to a nebuliser which generates an aerosol plume and to a patient interface. Upon inhalation by a patient ambient air is drawn into the device and flows counter-currently to the aerosol plume. However, the device is relatively large and cumbersome for use and complex to manufacture. It is also restricted to particular uses

STATEMENTS OF INVENTION

According to the invention there is provided an aerosol delivery device comprising a housing defining a chamber, the housing having:—

- a base;
- a top;
- a main body extending between the base and the top;
- an air inlet closed by an inlet valve, the air inlet being located adjacent to the base of the housing;
- a patient port for receiving a mouthpiece or a face mask, the mouthpiece or face mask having an exhaust outlet closed by an exhaust valve; and
- an aerosol port for receiving a vibrating mesh aerosol generating device, the aerosol port being located in a side of the main body of the housing for delivery of aerosol into the chamber between the inlet valve and the patient port,
- the inlet valve being breath actuatable for movement between an inspiration configuration in which the inlet valve is open and an exhalation configuration in which the inlet valve is closed.

In one embodiment the housing comprises a boss extending from the base of the housing and being spaced-apart inwardly of the main body of the housing to define a reception space.

In one case the inlet valve is mounted to the boss for movement between the open and closed configurations. The boss may comprise a raised region against which a portion of the inlet valve is seated. The raised region may be defined by a rim which extends at least partially around the boss.

In one embodiment the housing comprises an oxygen supply port for connection to a supply of oxygen. The oxygen supply port may be normally closed by the inlet valve. In one case the oxygen supply port is located within the margins of the boss.

In one embodiment a longitudinal axis through a center of the aerosol inlet port is substantially at right angles with respect to a longitudinal axis through the main body of the housing.

In one case a longitudinal axis through a center of the patient port is offset from a longitudinal axis through a center of the inlet. The main body of the housing may comprise a tapered transition section to the patient port.

The invention also provides an aerosol delivery system comprising an aerosol deliver device of the invention and a mouth piece or a face mask for connection to the patient port.

In a preferred embodiment the mouthpiece or face mask comprises an exhaust outlet closed by an exhaust valve, the inlet and exhaust valves being breath actuated from an inspiration configuration in which the inlet valve is open and the exhaust valve is closed to an exhalation configuration in which the inlet valve is closed and the exhaust valve is open.

In one case a longitudinal axis through a center of the patient port of the mouth piece subtends on angle of from 0° to 90° with a longitudinal axis of the main body of the housing. The angle may be approximately 60°.

In a further aspect the invention provides an aerosol delivery system further comprising a vibrating mesh aerosol generator for connection to the aerosol port for delivery of aerosol into inspiration gas flowing through the chamber when then inlet valve is open.

BRIEF DESCRIPTION OF THE DRAWINGS

The invention will be more clearly understood from the following description thereof, given by way of example in which:

FIG. 1 is an isometric, partially cut-away view of an aerosol delivery system according to the invention;

FIG. 2 is an isometric view of an aerosol delivery device of the invention forming part of the system of FIG. 1;

FIGS. 3 and 4 are cross sectional views of the aerosol delivery system of FIG. 1;

FIG. 5 is an isometric view of an air inlet end of the device with a valve removed;

FIGS. 6 and 7 are cross sectional views of the air inlet end of FIG. 5;

FIG. 8 is an isometric view of the air inlet end of the device with a valve in situ;

FIGS. 9 to 10 are elevational and cross sectional views of the air inlet end of FIG. 8; and FIGS. 11 to 13 are isometric views of the device and an associated face mask.

DETAILED DESCRIPTION

The invention provides a system for delivery of aerosol therapy to spontaneously breathing patients.

Referring to the drawings there is illustrated an aerosol delivery device according to the invention which comprises a housing 1 which defines a chamber 2. The housing has a base 3, a 30 top 4 and a main body 5 extending between the base 3 and the top 4. An ambient air inlet 6 is located adjacent to the base 3 and is normally closed by an inlet valve 7.

The housing also has a patient port 10 for receiving a mouthpiece 11 or a face mask 12. The mouthpiece 11 has an exhaust outlet 14 closed by an exhaust valve 15. Similarly, the face mask 12 has an exhaust outlet closed by an exhaust valve 16. Exhaled air is exhausted through the valves 15 and 16 to prevent recirculation through the chamber 2 which would adversely affect dose efficiencies.

The housing also has an aerosol port 20 for receiving a vibrating mesh aerosol generating device 25. The aerosol port 20 is located in a side of the main body of the housing 1 for delivery of aerosol into the chamber 2 between the inlet valve 7 and the patient port 10, generally perpendicular to the flow of air through the chamber 2.

The inlet valve 7 and the exhaust valves 15, 16 are one-way breath actuated and move from an inspiration configuration in which the inlet valve 7 is open and the exhaust valve 15,16 is closed to an exhalation configuration in which the inlet valve 7 is closed and the exhaust valve 15,16 is open.

The housing 1 comprises a boss 30 extending upwardly from the base 3. The boss is spaced-apart inwardly of the main body 5 of the housing 1 to define a reception space or well 31. This facilitates collection of any rain-out within the chamber 2. The inlet valve 7 is of a flexible polymeric material such as Elastosil R401-40 (Wacker, Munich, Germany) and has a receiver for mounting to a mounting element 33. The valve 7 is movable relative to the boss 30 between the open and closed configuration. The boss 30 also has a raised region which in this case is defined by a rim 35 which extends around the boss 30 to lift one section of the valve 7. This assists in preventing adhesion between the valve 7 and the boss 30 and facilitates opening of the valve even if the inhalation force applied is low.

The housing 2 also has an oxygen supply port 40 for connection to a supply of supplemental oxygen. In this case the oxygen supply port 40 is located in the base 3 of the device within the margins of the boss 30 and is normally closed by the inlet valve 7. Thus, the inlet valve occludes the oxygen port when no oxygen flow is connected, thus maximising device efficiency. When an oxygen supply is connected the valve 7 opens. This arrangement avoids the necessity for a separates cap or valve on the oxygen supply port and diffuses oxygen flow entering the chamber 2 which improves the efficiency of the device.

It will be noted that a longitudinal axis through a center of the aerosol delivery port 20 is substantially at right angles with respect to a longitudinal axis through the main body of the housing 1. This feature assists in reducing aerosol impaction and therefore maximises dose efficiency during changes in flow direction associated with inhalation and exhalation. It also facilitates nebuliser placement for cable management and device usability.

A longitudinal axis through a center of the patient port 10 is offset from a longitudinal axis through a center of the air inlet. This feature also assists in reducing aerosol impaction and therefore maximises dose efficiency. This optimum placement also minimises device size and therefore maximises usability.

The main body of the housing 1 comprises a tapered transition section 50 to the patient port 10. This provides minimum resistance to flow and minimises rain-out whilst maximising efficiency.

Figure 4:
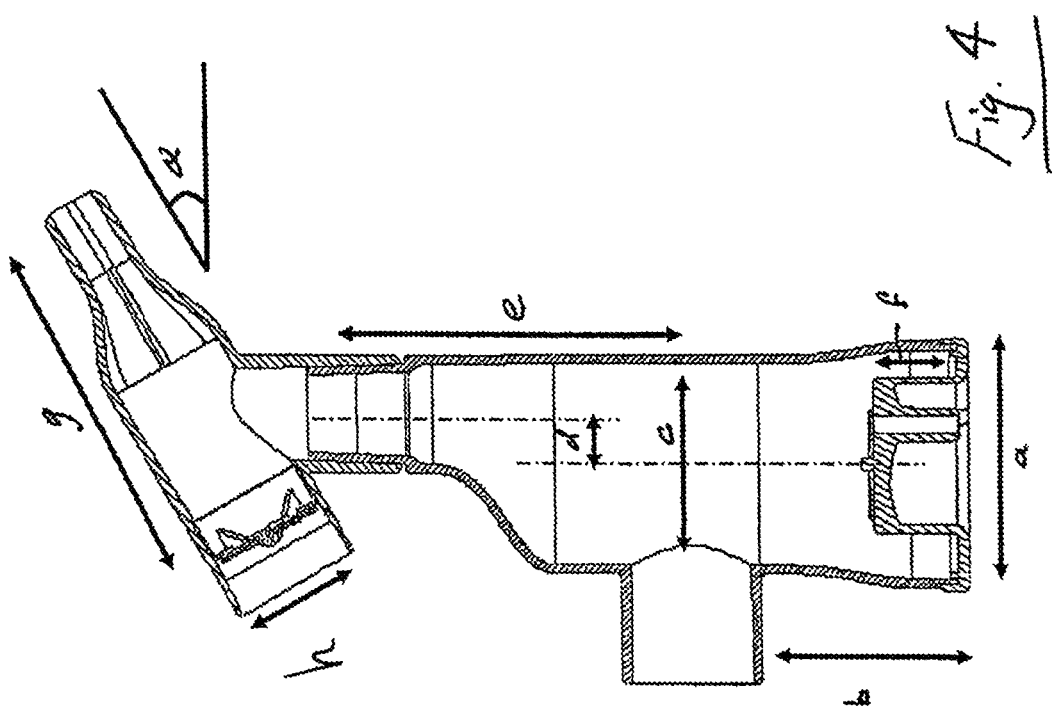
Figure 5:
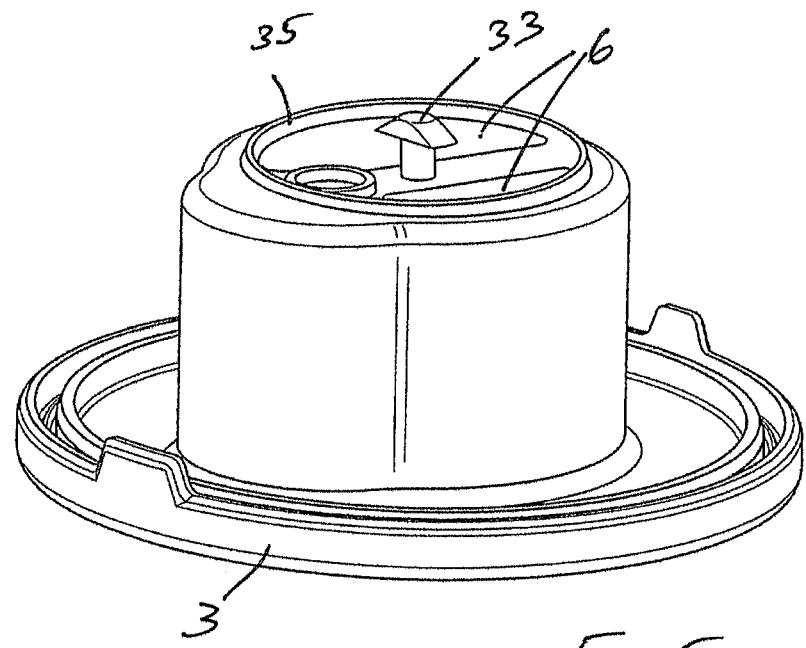
Figure 8:
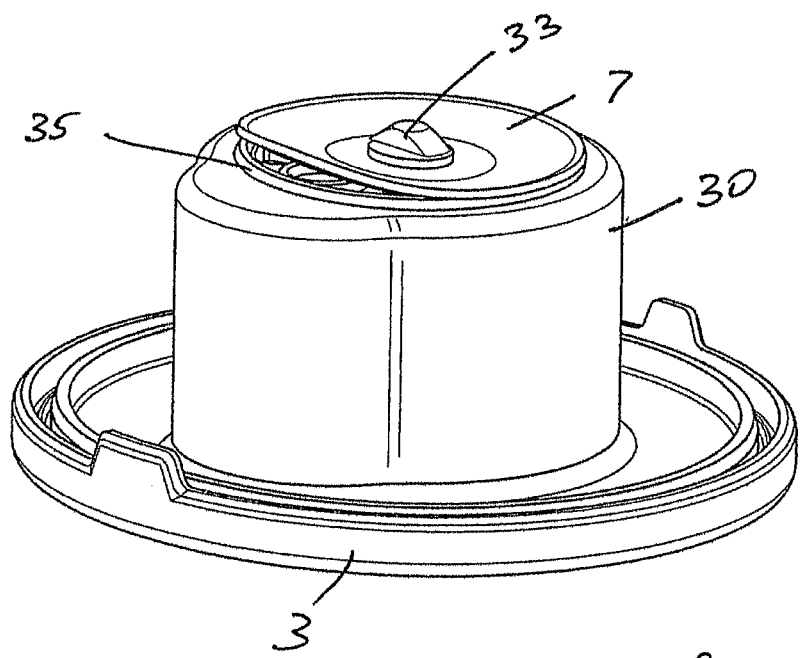
Figure 6:
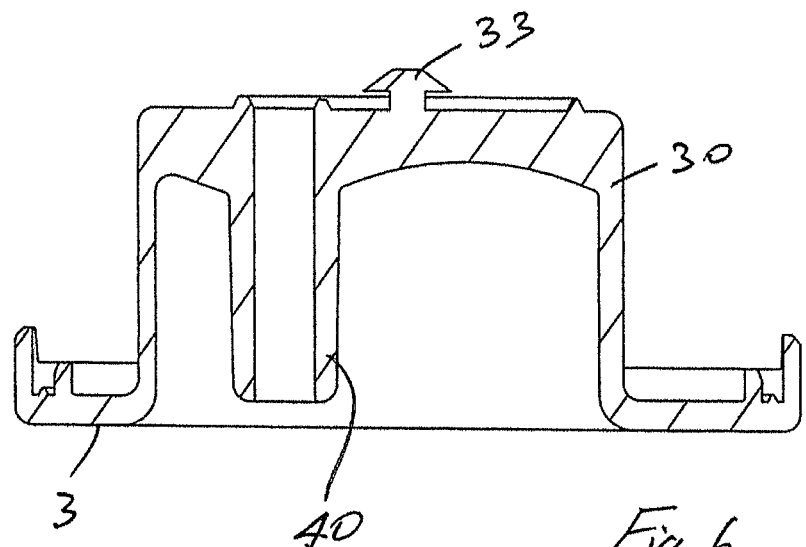
Figure 7:
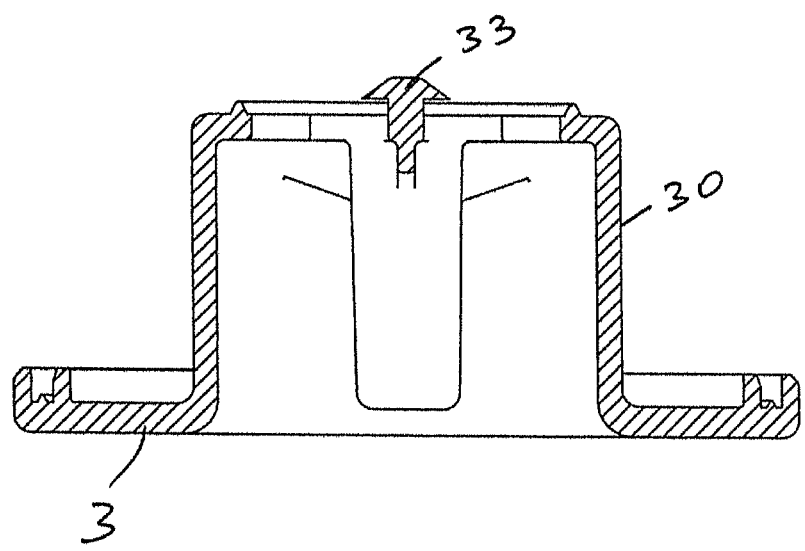
Figure 9:
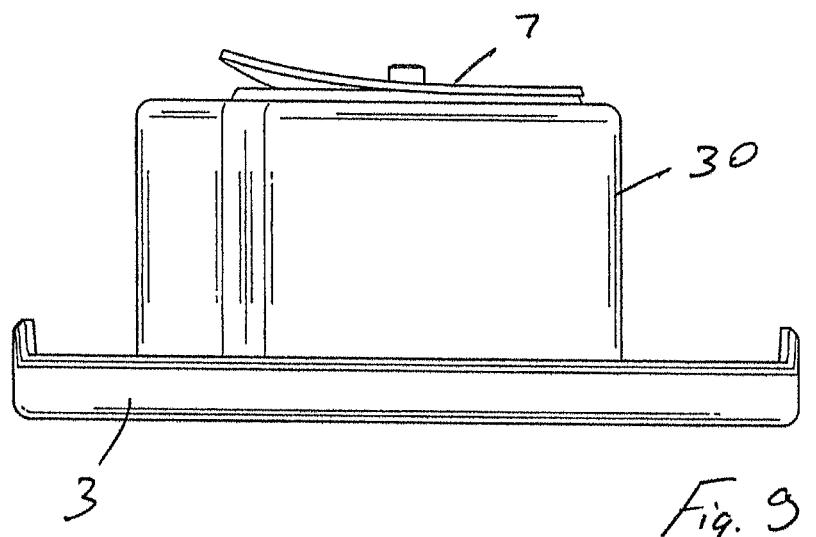
Figure 10:
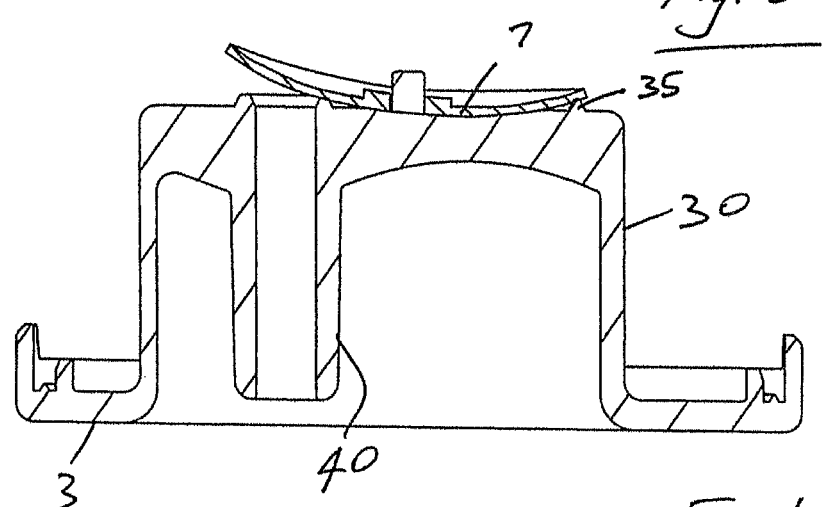
Figure 11:
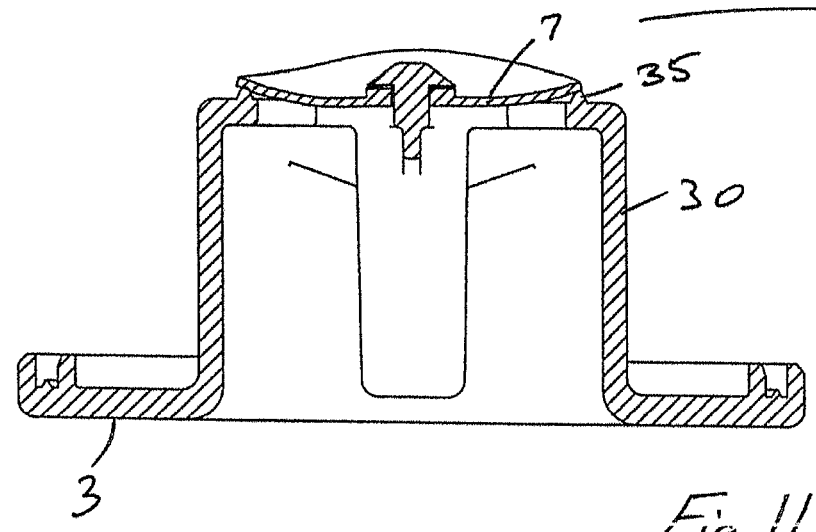
Figures 12, 13:
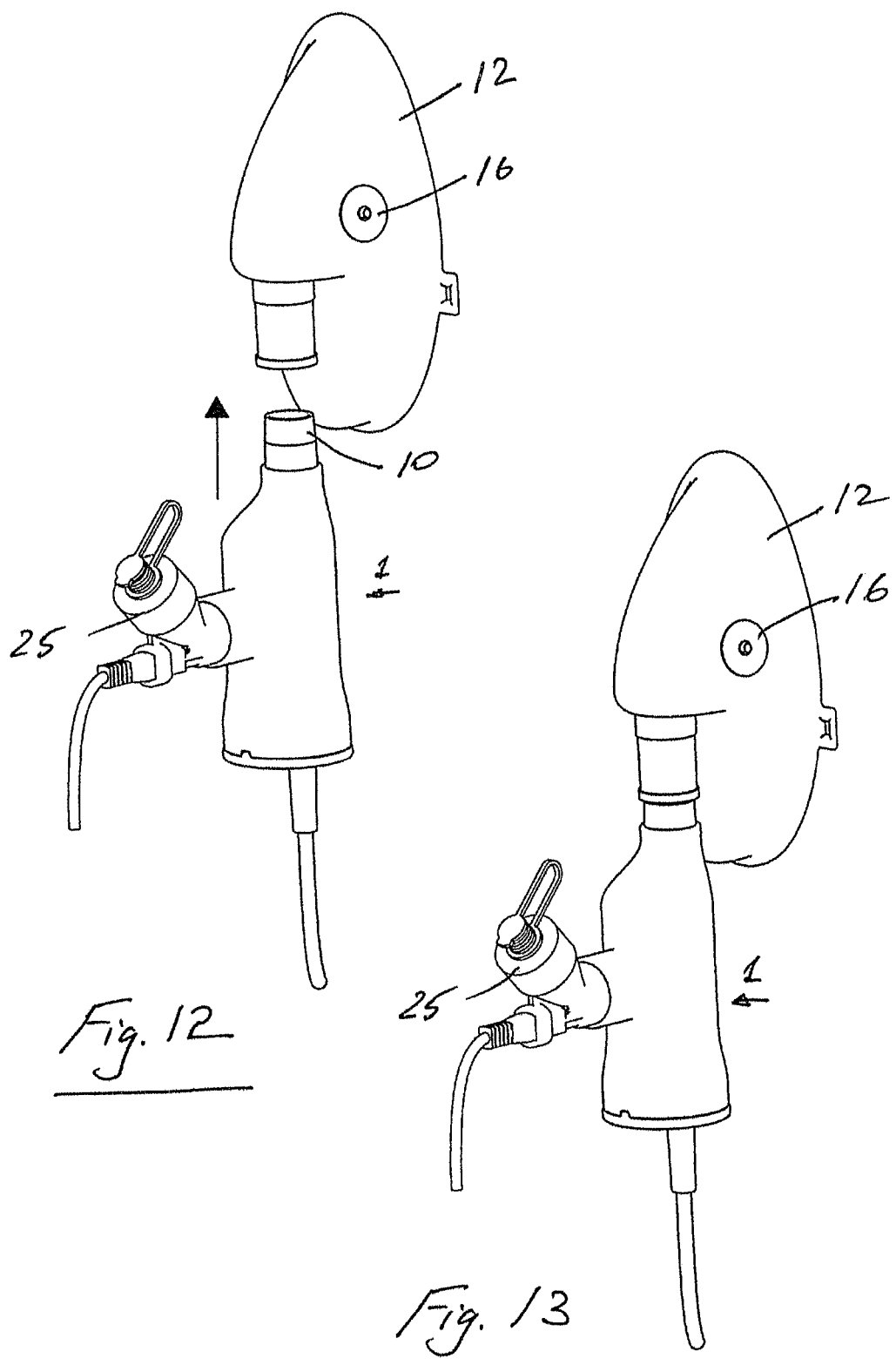

Referring in particular to FIG. 4, it will also be noted that a longitudinal axis through a center of the patient port of the mouth piece subtends an angle α of from about 0° to about 90°, in this case approximately 60° to the main body of the housing. This also maximises dose efficiency. Referring in particular to FIG. 4 the dimensions a to h are important in optimising device efficiency. The approximate values for these dimensions are as follows.

a range: 40-60 optimum approximately 46 mm
b range: 22-66 optimum approximately 39 mm
c range: 25-45 optimum approximately 37 mm
d range: 0-10 optimum approximately 9 mm
e range: 50-90 optimum approximately 67 mm
f range: 17-25 optimum approximately 17 mm
g range: 70-90 optimum approximately 70 mm
h range: 20-30 optimum approximately 24 mm In the invention high efficiency is achieved by:
Chamber design (i.e. diameter, length, etc.)
Neb positioning (i.e. perpendicular to chamber main axis, distance between neb and opposing wall and distance between neb and inlet valve)
Valves configuration to control the flow of air through the device
Angle of mouthpiece to chamber
Alignment of chamber outlet with bottom wall
Use of inlet valve to diffuse flow oxygen into the device
Rainout management is achieved by:
Inlet valve is located in a raised position ensure it does not contact rainout
Inlet valve seals on raised rim to reduce adhesion due to rainout
Inlet valve seal design to lift one section of valve to reduce the pressure differential required to open valve The system can be used with or without supplementary oxygen.

The aerosol generator 25 is a vibrating mesh type nebuliser as described in our WO2012/046220A, the entire contents of which are incorporated herein by reference.

Aerosol generators comprising a vibratable member and a plate body operably coupled to the vibratable member are known, the plate body has a top surface, a bottom surface, and a plurality of apertures extending from the top surface to the bottom surface. The apertures may be tapered such that when a liquid is supplied to one surface and the aperture plate is vibrated using the vibratable member, liquid droplets are ejected from the opposite surface. Details of such known systems are described for example in U.S. Pat. No. 6,235,177, US2007/0023547A, and U.S. Pat. No. 7,066,398, the entire contents of which are herein incorporated by reference.

The invention may be used to provide treatments for a variety of aliments using a variety of aerosolisable medicaments. The ailments may include pulmonary ailments such as ventilator-associated pneumonia, hospital-acquired pneumonia, community-acquired pneumonia, asthma, cystic fibrosis, mycobacterial infection, mucociliary clearance conditions, bronchitis, staph infection, fungal infections, viral infections, tuberculosis, protozoal infections, emphysema, hereditary emphysema, Chronic Obstructive Pulmonary Disease (COPD) and acute exacerbation of COPD, among others. The aerosolizable medicaments used to treat the ailments may include antitrypsins (such as alpha-1 antitrypsin), antibiotics, anti-infectives, antivirals, anti-oxidants, epithelium sodium channel blockers, bronchodilators, beta-antagonists (short and long acting) corticosteroids, leukotrienes, protease inhibitors, surfactants, and vaccines, among other medicaments. The ailments may further include non-pulmonary-related, such as systemic conditions, such as diabetes, cancer, immune diseases, cardiovascular conditions, metabolic diseases and the like.

The invention may be used in a method of treating a patient by administering to the patient any desirable nebulised dose of aerosol.

In some cases the method of treating a patient involves administering to the patient a discrete nebulised dose of aerosol comprising from 0.05 mL to about 50 mL of a medicament or greater than 50 mL when administering continuous aerosol therapy.

Also provided are methods of treatment by administering to a patient an aerosolised formulation comprising an anti-infective dissolved in an aqueous solution that is adjusted to a pH between about 3.0 and 10.5.

In some cases the medicament is administered continuously.

In other cases the medicament is administered intermittently.

The systems are configurable to administer aerosolised medicament, such as an anti-infective, to a spontaneous-breathing patient.

Substantially all of the device may be reused for multiple treatments with a single patient before disposing thereof.

The device may be used for only a single patient, then disposed.

A filter can be positioned at the exhaust outlet to capture exhausted drug.

The invention is not limited to the embodiments hereinbefore described, which may be varied in construction and detail.

The invention claimed is:

1. An aerosol delivery device, comprising:
a body defining a chamber and having a first end and a second end, a central longitudinal axis of the first end is in the same direction as a central longitudinal axis of the second end, wherein a diameter of the first end is larger than a diameter of the second end, the body including:
an air inlet located at the first end;
a patient port located at the second end;
a first side extending between the first and second ends; and
a second side opposite the first side, the second side including an aerosol port in fluid communication with the chamber and positioned between the first end and the second end, and
a patient interface located at the second end and in fluid communication with the patient port, and wherein a central longitudinal axis of the patient interface is angled at an obtuse angle with respect to the central longitudinal axis of the second end and
wherein the patient interface includes a mouthpiece having a patient opening therein and an exhaust outlet, and the patient opening is on an opposite side of the patient interface as the exhaust outlet.

2. The aerosol delivery device of claim 1, wherein the aerosol port defines an extension portion extending substantially perpendicular from the second side of the body.

3. The aerosol delivery device of claim 2, wherein the extension portion receives an aerosol generator device.

4. The aerosol delivery device of claim 1, further including a boss located at the first end.

5. The aerosol delivery device of claim 1, wherein a central longitudinal axis of the aerosol port is perpendicular to the central longitudinal axes of the first and second ends.

6. The aerosol delivery device of claim 1, wherein the central longitudinal axis of the patient interface is angled with respect to a central longitudinal axis of the patient port.

7. The aerosol delivery device of claim 1, wherein the patient interface includes an exhaust valve.

8. The aerosol delivery device of claim 1, further including an inlet valve located at the air inlet.

9. An aerosol delivery device, comprising:
a body defining a chamber and having a first end and a second end, wherein a diameter of the first end is larger than a diameter of the second end, the body including:
an air inlet located at the first end;
a patient port located at the second end;
a first side extending between the first and second ends; and
a second side opposite the first side, the second side including an aerosol port in fluid communication with the chamber, wherein the aerosol port defines an extension portion extending substantially perpendicular from the second side of the body; and
a patient interface coupled to the patient port by a coupling port so as to be in fluid communication with the patient port, and wherein the patient interface includes an exhaust valve and a mouthpiece having a patient opening therein and an exhaust outlet, and the patient opening and the exhaust valve are in line with one another and on opposite sides of the mouthpiece.

10. The aerosol delivery device of claim 9, wherein the extension portion is substantially cylindrical.

11. The aerosol delivery device of claim 10, wherein the extension portion receives an aerosol generator device.

12. The aerosol delivery device of claim 9, wherein a central longitudinal axis of the first end is in the same direction as a central longitudinal axis of the second end.

13. The aerosol delivery device of claim 9, further including an inlet valve located at the air inlet.

14. The aerosol delivery device of claim 9, wherein a central longitudinal axis of the patient interface is angled with respect to a central longitudinal axis of the second end.

15. The aerosol delivery device of claim 14, wherein the angle between the central longitudinal axis of the patient interface and the central longitudinal axis of the second end is obtuse.

16. The aerosol delivery device of claim 15, wherein the angle between the central longitudinal axis of the patient interface and the central longitudinal axis of the second end is on the first side.

17. An aerosol delivery device, comprising:
a body defining a chamber and having a first end and a second end, a central longitudinal axis of the first end is in the same direction as a central longitudinal axis of the second end, wherein a diameter of the first end is larger than a diameter of the second end, the body including:
an air inlet located at the first end;
an inlet valve located at the air inlet;
a patient port located at the second end;
a first side extending between the first and second ends; and
a second side opposite the first side, the second side including an aerosol port in fluid communication with the chamber and positioned between the first end and the second end, a central longitudinal axis of the aerosol port is perpendicular to the central longitudinal axes of the first and second ends, wherein the aerosol port defines an extension portion extending substantially perpendicular from the second side of the body; and
a patient interface coupled to the second end and in fluid communication with the patient port, the patient interface including an exhaust valve, and
wherein the patient interface includes a mouthpiece having a patient opening therein and the patient opening is on an opposite side of the patient interface as the exhaust valve.

18. The aerosol delivery device of claim 17, wherein the extension portion is substantially cylindrical.

19. The aerosol delivery device of claim 17, wherein the extension portion is configured to receive an aerosol generator device.

* * * * *